(12) United States Patent
Avery et al.

(10) Patent No.: US 9,494,264 B2
(45) Date of Patent: Nov. 15, 2016

(54) CODED DRUG RESERVOIR CONNECTION ELEMENT WITH HINGE

(75) Inventors: Richard James Vincent Avery, Chipping Campden (GB); Joseph Butler, Rugby (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 736 days.

(21) Appl. No.: 13/812,951

(22) PCT Filed: Aug. 11, 2011

(86) PCT No.: PCT/EP2011/063839
§ 371 (c)(1),
(2), (4) Date: Apr. 22, 2013

(87) PCT Pub. No.: WO2012/020083
PCT Pub. Date: Feb. 16, 2012

(65) Prior Publication Data
US 2014/0163468 A1 Jun. 12, 2014

Related U.S. Application Data

(60) Provisional application No. 61/373,384, filed on Aug. 13, 2010.

(30) Foreign Application Priority Data

Oct. 26, 2010 (EP) ..................................... 10188847

(51) Int. Cl.
*A61M 5/50* (2006.01)
*F16L 15/08* (2006.01)
(Continued)

(52) U.S. Cl.
CPC .............. *F16L 15/08* (2013.01); *A61J 1/1412* (2013.01); *A61J 1/1475* (2013.01); *A61M 5/24* (2013.01);
(Continued)

(58) Field of Classification Search
CPC ...... A61J 1/1412; A61J 1/1425; A61J 1/062; A61J 1/2048; A61M 5/31; A61M 5/24; A61M 5/347; A61M 2205/6045; A61M 2005/2488; A61M 2005/2492; A61M 2205/276; A61M 2005/2433; A61M 2005/244; A61M 2005/2485; A61M 2205/582
USPC ............... 215/237, 249, 250, 272, 273, 277; 604/189, 240, 241
See application file for complete search history.

(56) References Cited

U.S. PATENT DOCUMENTS 4,205,754 A * 6/1980 Nielsen ................ B65D 51/002
215/249
4,417,890 A * 11/1983 Dennehey ............. A61M 39/20
138/89

(Continued)

FOREIGN PATENT DOCUMENTS

DE 2100287 A1 6/1972
EP 1930038 A2 11/2008
WO 2008071804 A2 6/2008

*Primary Examiner* — Gerald Landry, II
(74) *Attorney, Agent, or Firm* — McDonnell Boehnen Hulbert & Berghoff LLP (57) ABSTRACT

A cap for a cartridge having a bead at the distal end is disclosed. The cap comprises:
a main body having a proximal end, a distal end, and a bore that receives the cartridge, the main body further comprising a first segment and a second segment; and a retention feature on the main body suitable for snapping under the bead of the cartridge for securing the cap to the cartridge.

22 Claims, 4 Drawing Sheets

(51) Int. Cl.
  *A61J 1/14* (2006.01)
  *A61M 5/24* (2006.01)
  *A61M 5/34* (2006.01)
  *A61M 5/315* (2006.01)

(52) U.S. Cl.
  CPC ........... *A61M 5/344* (2013.01); *A61M 5/5086* (2013.01); *A61J 1/1418* (2015.05); *A61J 1/1481* (2015.05); *A61J 2205/40* (2013.01); *A61M 5/31551* (2013.01); *A61M 5/347* (2013.01); *A61M 2005/2411* (2013.01); *A61M 2005/2474* (2013.01); *A61M 2205/276* (2013.01); *A61M 2205/6045* (2013.01); *A61M 2205/6081* (2013.01)

(56) References Cited

U.S. PATENT DOCUMENTS

| | | | | |
|---|---|---|---|---|
| 4,614,267 A * | 9/1986 | Larkin | | A61J 1/2089 206/219 |
| 5,088,612 A * | 2/1992 | Storar | | B65D 47/0819 215/235 |
| 5,554,134 A * | 9/1996 | Bonnichsen | | A61M 5/24 604/232 |
| 5,693,027 A * | 12/1997 | Hansen | | A61M 5/24 604/200 |
| 6,152,320 A * | 11/2000 | Hierzer | | B65D 47/0809 215/235 |
| 6,648,859 B2 * | 11/2003 | Bitdinger | | A61M 5/24 604/218 |
| 7,637,899 B2 * | 12/2009 | Woolston | | A61M 5/24 604/403 |
| 7,766,197 B2 * | 8/2010 | Getsy | | B65D 47/265 220/253 |
| 7,988,678 B2 * | 8/2011 | Monson | | A61M 5/344 604/200 |
| 2002/0022805 A1 * | 2/2002 | Lane | | A61M 5/31581 604/210 |
| 2003/0004466 A1 | 1/2003 | Bitdinger et al. | | |
| 2003/0078195 A1 | 4/2003 | Kristensen et al. | | |
| 2006/0131344 A1 * | 6/2006 | Brass | | B05C 17/0133 222/390 |
| 2007/0060897 A1 * | 3/2007 | Wang | | A61M 5/24 604/232 |
| 2009/0069753 A1 * | 3/2009 | Ruan | | A61M 5/3202 604/192 |
| 2009/0259197 A1 * | 10/2009 | Christiansen | | A61M 5/24 604/208 |
| 2010/0094241 A1 * | 4/2010 | Remde | | A61J 1/2089 604/403 |
| 2012/0123347 A1 * | 5/2012 | Boyd | | A61M 5/24 604/192 |

* cited by examiner

CODED DRUG RESERVOIR CONNECTION ELEMENT WITH HINGE

CROSS REFERENCE TO RELATED APPLICATIONS

The present application is a U.S. National Phase Application pursuant to 35 U.S.C. §371 of Inter rational Application No. PCT/EP2011/063839 filed Aug. 11, 2011, which claims priority to U.S. Patent Application No. 61/373,384 filed Aug. 13, 2010 and European Patent Application No. 10188847.7 filed Oct. 26, 2010. The entire disclosure contents of these applications are herewith incorporated by reference into the present application.

TECHNICAL DISCLOSURE OF INVENTION

The present disclosure is generally directed to reservoirs, particularly reservoirs containing a medicament. More particularly, the disclosure is generally directed to a segmented cap for use with a reservoir and a reservoir holder so as to prevent unwanted reservoir cross use. As just one example, such medicament reservoirs may comprise an ampoule, a cartridge, a vial, or a pouch, and may be used with a medical delivery device. Exemplary medical delivery devices include, but are not limited to, syringes, pen type injection syringes, pumps, inhalers, or other similar injection or infusing devices that require at least one reservoir containing at least one medicament.

BACKGROUND

Medicament reservoirs such as ampoules, cartridges, or vials are generally known. Such reservoirs are especially used for medicaments that may be self-administered by a patient. For example, with respect to insulin, a patient suffering from diabetes may require a certain amount of insulin to either be injected via a pen type injection syringe or infused via a pump. With respect to certain known reusable pen type drug delivery devices, a patient loads a cartridge containing the insulin into a proximal end of a cartridge holder. After the cartridge has been correctly loaded, the user may then be called upon to select a dose of medicament. Multiple doses may be dosed from the cartridge. Where the drug delivery device comprises a reusable device, once the cartridge is empty, the cartridge holder is disconnected from the drug delivery device and the empty cartridge is removed and replaced with a new cartridge. Most suppliers of such cartridges recommend that the user dispose of the empty cartridges properly. Where the drug delivery device comprises a disposable device, once the cartridge is empty, the user is recommended to dispose of the entire device.

Such known self-administration systems requiring the removal and reloading of empty cartridges have certain limitations. For example, in certain generally known systems, a user simply loads a new cartridge into the delivery system without the drug delivery device or without the cartridge having any mechanism of preventing cross use of an incorrect cartridge. That is, the drug delivery device does not have a mechanism for determining if the medicament contained in the cartridge is indeed the correct type of medicament to be administered by the patient. Alternatively, certain known drug delivery devices do not present a mechanism for determining if the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short acting insulin in lieu of a long insulin could result in injury or even death.

Another concern that may arise with such disposable cartridges is that these cartridges are manufactured in essentially standard sizes and must comply with certain recognized local and international standards. Consequently, such cartridges are typically supplied in standard sized cartridges (e.g., 3 ml cartridges). Therefore, there may be a variety of cartridges supplied by a number of different suppliers and containing different medicaments but they may fit a single drug delivery device. As just one example, a first cartridge containing a first medicament from a first supplier may fit a medical delivery device provided by a second supplier. As such, a user might be able to load and then dispense an incorrect medicament (such as a rapid or basal type of insulin) into a drug delivery device without being aware that the medical delivery device was perhaps neither designed nor intended to be used with such a cartridge.

As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

There is, therefore, a general need to physically dedicate or mechanically code a cartridge to its drug type and design an injection device that only accepts or works with the dedication or coded features provided on or with the cartridge so as to prevent unwanted cartridge cross use. Similarly, there is also a general need for a dedicated cartridge that allows the medical delivery device to be used with only an authorized cartridge containing a specific medicament while also preventing undesired cartridge cross use.

There is also a general need to provide a dedicated cartridge that is difficult to tamper with so that the cartridge may not be compromised in that the cartridge can be used with an unauthorized drug or drug delivery device. Because such cartridges may be difficult to tamper with, they may also reduce the risk of counterfeiting: i.e., making it more difficult for counterfeiters to provide unregulated counterfeit medicament carrying products. It is an aim to provide means which reduces the potential risk of a user using an incorrect drug type cartridge.

SUMMARY

This aim is achieved by a cap for a cartridge having a bead at the distal end. The cap comprises a main body having a proximal end, a distal end, and a bore that receives the cartridge, the main body further comprising a first segment and a second segment. A retention feature is provided on the main body which is suitable for snapping under the bead of the cartridge for securing the cap to the cartridge.

The cap may serve as adaptor which is used with a cartridge or reservoir having a bead and a neck. The cap may be a adaptor top or vial adaptor. The cap may be used for securing the cartridge or reservoir within a drug delivery device. Preferably, the bore defines a diameter.

The distal end of the drug delivery device refers to that end of the drug delivery device which is closest to a dispensing end of the drug delivery device. The proximal end of the device refers to that end of the device which is furthest away from the dispensing end of the device. The distal end of the cartridge is the dispensing end of the cartridge. The distal portion of the cap refers to the portion that in use is closest to the distal end of the cartridge. The distal portion of the cap is the opposite portion.

In one embodiment the first segment is attached to the second segment by a hinge. The hinge may extend along at least a portion of a length of the main body of the cap from the proximal end to the distal end. Alternatively, the hinge may be located at the distal end of the main body. In one embodiment the hinge extends in a transverse direction. The hinge may extend along the radius on the distal top of the main body. Alternatively the hinge may extend on the distal top along another chord. The proximal portion of the main body may be moveable. In one embodiment the hinge is located at the proximal end of the main body.

The retention feature may be provided on the proximal end of the main body. In one embodiment the retention feature is a protrusion. In one embodiment the cap comprises at least one fastening mechanism for securing the first segment to the second segment. In one embodiment the retention feature includes at least one fastening mechanism for securing the first segment to the second segment, wherein the fastening mechanism may comprise a male element and a female element.

On embodiment of the cap further comprises a first coding feature that cooperates with a corresponding second coding feature of the drug delivery device, which enables securing the reservoir of the drug delivery device.

In one embodiment, the main body further comprises a thread configured for receiving a threaded needle hub, which enables attaching the needle hub. The first segment may comprise a first threaded portion and the second segment may comprise a second threaded portion.

In one embodiment the first segment and the second segment comprise a unitary main body. According to an exemplary arrangement, a cap for securing a reservoir within a drug delivery device is disclosed. The cap includes a main body having a proximal end, a distal end, and a bore defining a diameter that receives the reservoir. The main body includes a first segment and a second segment. These two segments may comprise a unitary main body. The cap also has a retention feature on the proximal end of the main body for securing the cap to the reservoir.

One embodiment of a drug delivery device comprises a dose setting mechanism; a reservoir holder or cartridge holder secured to the dose setting mechanism and a reservoir or cartridge contained within the reservoir holder or cartridge holder. A cap is secured to the reservoir or cartridge. The cap comprises a main body coupled to the reservoir or cartridge and having a proximal end, a distal end, and a bore defining a diameter that receives the reservoir or cartridge. The main body further comprises a first segment and a second segment; and a retention feature on the main body for securing the cap to the reservoir or cartridge.

In one embodiment, the first segment of the cap is attached to the second segment by a hinge. The hinge may extend along at least a portion of a length of the main body of the cap from the proximal end to the distal end. In one embodiment the hinge is located at the proximal end of the main body. A lower proximal portion of the main body may be moveable. In an alternative embodiment the hinge may be located at the distal end of the main body.

In one embodiment of the drug delivery device the retention feature may be a protrusion. The retention feature may include at least one fastening mechanism for securing the first segment to the second segment. One embodiment of the fastening mechanism includes a male element and a female element.

One embodiment of the drug delivery device further comprises a first coding feature that cooperates with a corresponding second coding feature of the drug delivery device so as to secure the reservoir to the drug delivery device.

In one embodiment of the drug delivery device the first segment of the cap comprises a first threaded portion and the second segment of the cap comprises a second threaded portion. The first segment and the second segment of the cap may comprise a unitary main body.

In another arrangement, a drug delivery device is provided. The drug delivery device includes a dose setting mechanism, a reservoir holder secured to the dose setting mechanism, a reservoir contained within the reservoir holder, and a cap for securing the reservoir within the reservoir holder. The cap includes a main body coupled to the reservoir and a proximal end, a distal end, and a bore defining a diameter that receives the reservoir. The main body also includes a first segment and a second segment. The cap also has a retention feature on the proximal end of the main body for securing the cap to the reservoir.

The terms "medicament", "medication" and "drug", as used herein, preferably mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N- palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group-Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

These as well as other advantages of various aspects will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which:

FIG. 1b illustrates a cartridge that may be loaded into a cartridge holder of the pen type drug delivery device illustrated in FIG. 1a;

FIG. 2a illustrates an example cap for use with a cartridge that may be used with a pen type drug delivery device, such as the drug delivery device illustrated in FIG. 1a;

FIG. 2b illustrates a bottom (or proximal end) view of the cap shown in FIG. 2a;

DETAILED DESCRIPTION

Figure 1A:
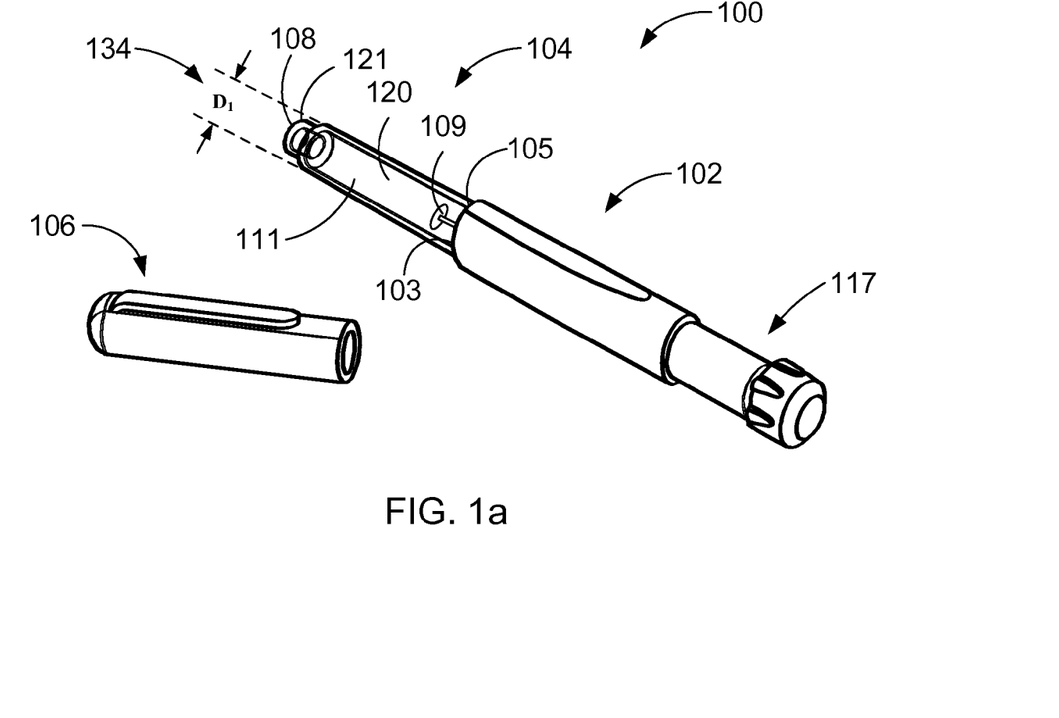
FIG. 1a illustrates an exemplary pen type drug delivery device.

Referring to FIG. 1a, there is shown a drug delivery device 100 in the form of a pen type syringe. This drug delivery device 100 comprises a dose setting mechanism 102, a reservoir or cartridge holder 104, and a removable cap 106. A proximal end 105 of the cartridge holder 104 and a distal end 103 of the dose setting mechanism 102 are removably secured together. The pen type syringe may comprise a re-usable or a disposable pen type syringe. Where the syringe comprises a re-usable device, the cartridge holder 104 and the dose setting mechanism 102 are removably coupled together. In a disposable device, they may be permanently coupled together. In FIG. 1a, the dose setting mechanism 102 comprises a piston rod 109, such as a threaded piston rod that rotates when a dose is injected.

To inject a previously set dose, a double ended needle assembly (not shown) is attached to a distal end 108 of the cartridge holder 104. Preferably, the distal end 108 of the cartridge holder 104 comprises a thread 121 (or other suitable connecting mechanism such as a snap lock, snap fit, form fit, or bayonet lock mechanism) so that the needle assembly may be removably attached to the distal end 108 of the cartridge holder 104. When the drug delivery device 100 is not in use, the removable cap 106 can be releasably retained over the cartridge holder 104.

Figure 1B:
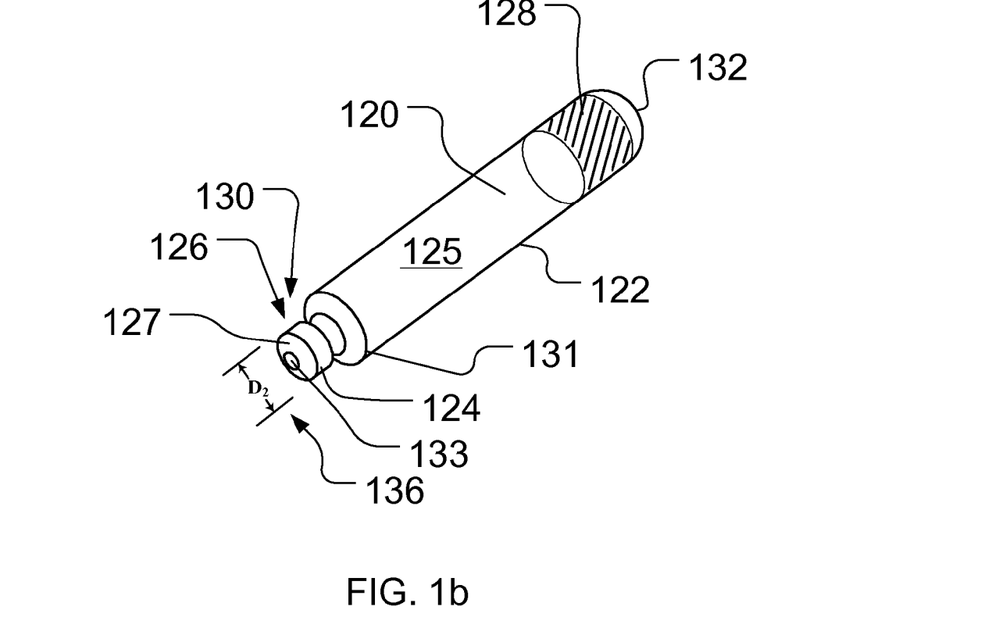

An inner cartridge cavity 111 defined by the cartridge holder 104 is dimensioned and configured to securely receive and retain a reservoir or cartridge 120. In an alternate embodiment, the cartridge 120 is inserted directly into the drug delivery device 100 without the use of a cartridge holder 104. FIG. 1b illustrates a perspective view of the cartridge 120 that may be used with the drug delivery device 100 illustrated in FIG. 1a. The cartridge 120 includes a generally tubular barrel 122 extending from a distal end 130 to a proximal end 132. The distal end 130 is defined by an inwardly converging shoulder 131.

At the distal end 130, the cartridge 120 includes a smaller diameter neck 126 and this neck 126 projects distally from the shoulder 131 of the barrel 122. Preferably, this smaller diameter neck 126 is provided with a large diameter annular bead and this bead extends circumferentially thereabout at the extreme distal end of the neck 126. A pierceable septum or seal 133 is securely mounted across the open distal end defined by the neck 126. The seal 133 may be held in place by a metallic sleeve or ferrule 124. This ferrule 124 may be crimped around the circumferential bead at the distal end of the neck 126. The medicament 125 is pre-filled into the cartridge 120 and is retained within the cartridge 120, in part, by the pierceable seal 133, the metallic sleeve or ferrule 124, and the stopper 128. The stopper 128 is in sliding fluid-tight engagement with the inner tubular wall of the barrel 122. Axially directed forces acting upon the stopper 128 during dose injection or dose administration urges the medication 125 from the cartridge 120 though a double ended needle mounted onto the distal end 108 of the cartridge holder 104 and into the injection site. Such axially forces may be provided by the piston rod 109.

A portion of the cartridge holder 104 defining the cartridge holder cavity 111 is of substantially uniform diameter represented in FIG. 1a by D1 134. This diameter D1 134 is preferably slightly greater than the diameter D2 136 of the cartridge 120. The interior of the cartridge holder 104 includes an inwardly-extending annual portion or stop that is dimensioned to prevent the cartridge 120 from moving within the cartridge holder 104. In this manner, when the cartridge 120 is loaded into the cavity 111 of the cartridge holder 104 and the cartridge holder 104 is then connected to the dose setting mechanism 102, the cartridge 120 will be securely held within the cartridge cavity 111. More particularly, the neck 126 and ferrule 124 of the cartridge 120 are inserted in a proximal to distal direction into the open proximal end 105 of the cartridge holder 104 with the ferrule 124 eventually passing entirely into the cartridge holder 104. With the cartridge holder 104 removably coupled to the dose setting mechanism 102, the proximal end 132 of the cartridge 120 will typically abut a stop provided by the dose setting mechanism 102.

A number of doses of a medicament 125 may be dispensed from the cartridge 120. Preferably, the cartridge 120 contains a type of medicament 125 that must be administered often, such as one or more times a day. One such medicament 125 is insulin. A movable piston (not shown) is retained in a first end or proximal end 132 of the cartridge 120 and receives an axial force created by the piston rod 109 of the dose setting mechanism 102.

The dose setting mechanism 102 comprises a dose setter 117 at the proximal end of the dose setting mechanism 102. In one preferred arrangement, the dose setter 117 is rotated to set a dose. To administer this set dose, the user attaches the needle assembly (not shown) comprising a double ended needle on the distal end 108 of the cartridge holder 104. In this manner, the needle assembly pierces the seal 133 of the cartridge 120 and is therefore in liquid communication with the medicament 125. The user pushes on the dose setter 117 to inject the set dose. The same dose setting and dose administration procedure is followed until the medicament 125 in the cartridge 120 is expended and then a new cartridge 120 must be loaded in the drug delivery device 100. To exchange an empty cartridge 120, the user is called upon to remove the cartridge holder 104 from the dose setting mechanism 102.

Figure 2A:
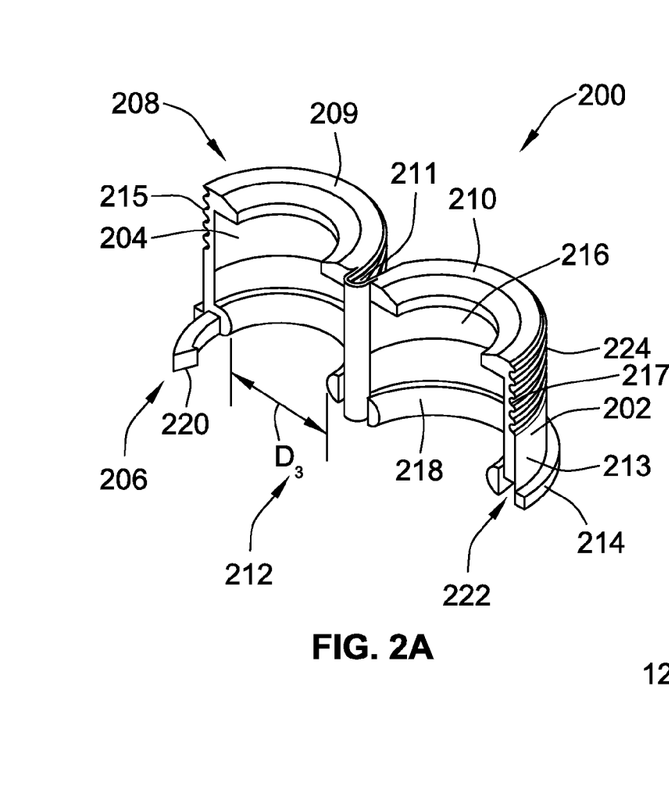
Figure 2B:
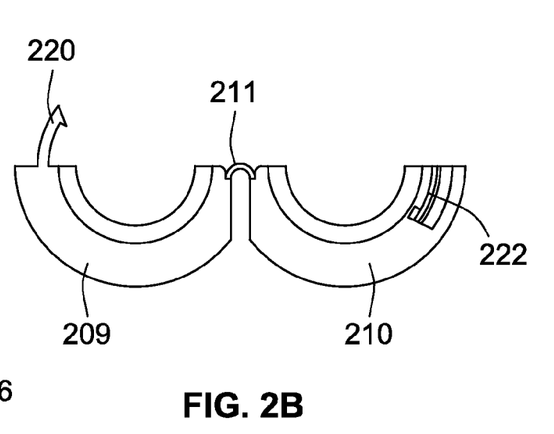

FIG. 2a illustrates a first embodiment of an example segmented cap 200 for use with a cartridge 120 or cartridge holder 104 that may be used with a pen type drug delivery device 100, such as the drug delivery device 100 illustrated in FIG. 1a. The cap 200 may also be mechanically coded to the cartridge holder 104 to ensure that the correct cartridge 120 is used with the correct cartridge holder 104 and drug delivery device 100.

Figure 3:
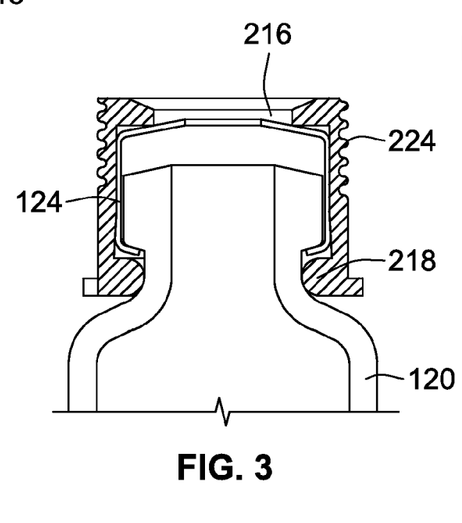
FIG. 3 illustrates the cap shown in FIG. 2a secured to a cartridge.

The cap 200 has a main body 202 and may include a bore 204 that extends from a proximal end 206 to a distal end 208 of the main body 202. The main body 202 may be separated into first and second segments 209, 210, which may be connected by a longitudinal hinge 211 that extends along at least a portion of a length of the cap 200 from the proximal end 206 to the distal end 208. Alternatively, the first and second segments 209, 210 may be independent from each other, and may be connected together during installation by snap fit features, adhesive, or welding, for example. As illustrated, the first segment 209 has a first threaded portion 215 and the second segment 210 has a second threaded portion 217. When connected together during installation, the first threaded portion 215 and the second threaded portion 217 form an outer thread 224 (see, e.g., FIG. 3). If these threaded portions 215, 217 of these two segments 209, 210 are misaligned with each other, it may be difficult to screw a needle onto the cap 200. To reduce this problem, the mating edges located on the proximal end 206 of the cap 200 may be recessed with a chamfer.

When the cap 200 is in use, the bore 204 of the first segment 209 is placed over a ferrule 124 located at the distal end 130 of a cartridge 120, such as ferrule 124 on cartridge 120 shown in FIG. 1b, and the second segment 210 is pushed together with the first segment 209 to surround all or part of the ferrule 124. Preferably, the main body 202 has a diameter D3 212 that is slightly larger than the diameter D2 of the ferrule 124 of the cartridge 120. Each segment 209, 210 of the cap 200 further comprises an axially extending wall 213 that extends from a flange 214 located near the proximal end 206 of the main body 202. These axially extending walls 213 extend towards the distal end 208 of the main body 202.

Near the distal end 208, the cap 200 may be provided with a pass through 216. In one arrangement, the pass through 216 is sized and configured so that, when the cap 200 is placed over the ferrule 124 of the cartridge 120 and the segments 209, 210 are secured together, the pass through 216 will expose a portion of the ferrule 124 of the cartridge 120 and will provide access to at least a portion of the pierceable seal 133 of the cartridge 120.

Near the proximal end 206, the cap 200 may include a retention feature 218. The retention feature 218 may comprise a protrusion located within the bore 204 of the cap 200. The retention feature 218 may be located on one or both of the first 209 and second 210 segments of the cap 200. The retention feature 218 functions to secure the cap 200 to the cartridge 120. Therefore, the retention feature 218 has an inner diameter that is smaller than the outer diameter of the ferrule 124, making removal of the cap 200 from the cartridge 120 more difficult. Although the retention feature 218 is depicted as extending around the full diameter D3 212 of the cap 200, it should be understood that the retention feature 218 may extend only around a portion of the diameter 212 of the cap 200, or may be comprised of one or more separate features. The cap 200 may also include other suitable fastening features to secure the cap 200 to the drug delivery device 100 or to the cartridge holder 104. For example, the cap 200 may fasten directly to the dose setting mechanism 102 such as using a bayonet lock or alternatively, it may clip into the cartridge holder 104 by way of a snap lock or a snap fit.

The retention feature 218 may further include a fastening mechanism. The fastening mechanism may comprise a male element 220 which may be connected to a female element 222 to secure the first segment 209 to the second segment 210. Although the male element 220 is shown on the first segment 209 and the female element 222 is shown on the second segment 210, it should be understood that the elements 220, 222 may be reversed. Furthermore, it should be understood that any suitable fastening mechanism may be used to secure the first segment 209 to the second segment 210.

In one arrangement, the cap 200 is intended for use with a standard double ended needle (not shown) wherein this needle comprises a hub having an internal thread. As such, an outer surface of the axially extending wall 213 of the main body 202 is provided with an outer thread 224 that receives such a hub of the double ended needle. Such an outer thread 224 could comprise a single or a double start outer thread. In addition, when such double ended needle is mounted onto the cap 200, the piercing distal needle projects through the pass through 216 and into the pierceable seal 133 of the cartridge 120.

The cap 200 may further include interlocking features to prevent rotation of the cap 200 relative to the cartridge holder 104. The interlocking features may comprise protrusions with a triangular section pointed towards the distal end 208. Alternatively, rotation of the cap 200 may be prevented by friction between the cap 200 and cartridge holder 104.

In another embodiment, the cap 200 may be provided with at least one alignment feature (not shown), for example small protrusions or grooves, to ensure that both segments 209, 210 of the cap 200 are correctly aligned when secured together. It should be understood that any suitable alignment features may be used.

In another arrangement, cap 200 may also include a first coding feature (not shown). The first coding feature may allow the cap 200 to be mechanically coded and cooperate with a second corresponding coding feature on the drug delivery device 100. The second coding feature may alternatively be located on the cartridge holder 104. Alternatively, the coding feature may comprise different colors of the cap 200 to distinguish between different drugs.

One advantage of the segmented cap 200 is that the cap 200 is tamper-evident. Removal of the cap 200 may damage the retention feature 218, preventing the cap 200 from being attached to another cartridge 120.

Figure 4:
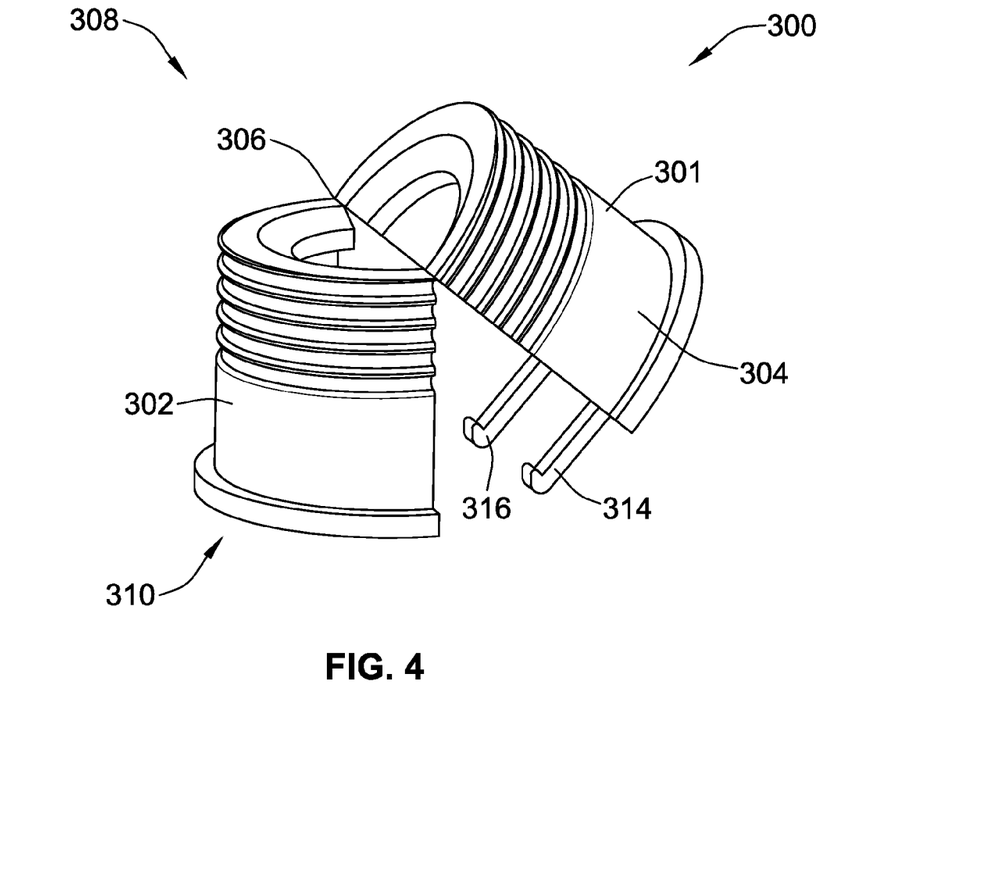
FIG. 4 illustrates a second embodiment of an cap for use with a cartridge.
Figure 5:
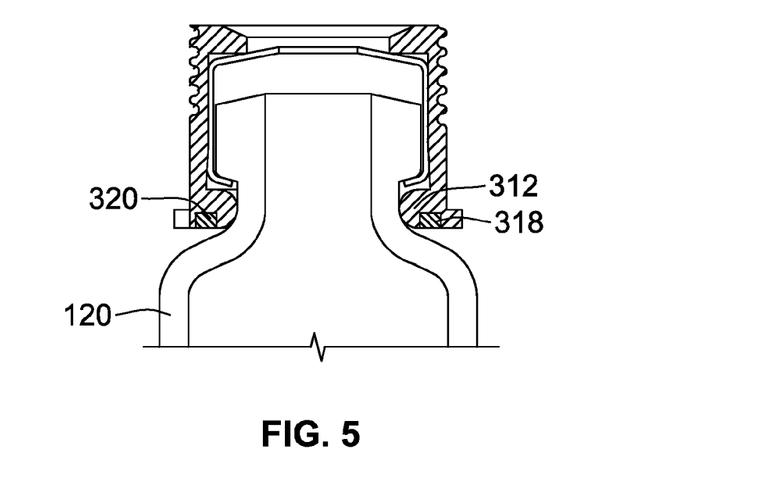
FIG. 5 illustrates the cap shown in FIG. 4 secured to a cartridge.

Another embodiment of an example cap 300 having a distal end 308 and a proximal end 310 is shown in FIGS. 4 and 5. In this embodiment, cap 300 may include a main body 301 having first and second segments 302, 304. The cap 300 has substantially the same structure as cap 200, except that cap 300 includes a transverse hinge 306 at the distal end 308 of the cap 300. Further, the cap 300 may include a retention feature 312, shown in FIG. 5, which may be a protrusion located within the bore of the cap 300. The retention feature 312 may be located on both the first 302 and second 304 segments of the cap 300. The retention feature 312 may function in the same manner as retention feature 218 described above with respect to cap 200.

The retention feature 312 may further include a fastening mechanism to secure the first segment 302 of the cap 300 to the second segment 304. The fastening mechanism may include at least one first male element 314 which may be connected to at least one first female element 318 (shown in FIG. 5). The retention feature 312 may also include a second male element 316 that mates with a second female element 320 to further secure the first segment 302 to the second segment 304. Although the male elements 314, 316 are shown on the first segment 302 and the female elements 318, 320 are shown on the second segment 304, it should be understood that the elements may be reversed. Furthermore, it should be understood that any suitable fastening mechanism may be used to secure the first segment 302 to the second segment 304.

Figure 6:
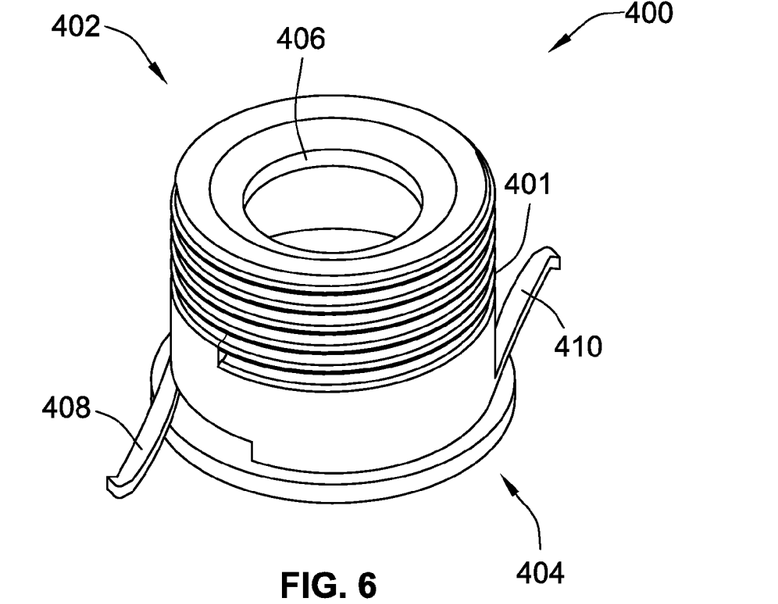
FIG. 6 illustrates another embodiment of a cap for use with a cartridge.

FIG. 6 shows yet another embodiment of a cap 400. The cap 400 may include a main body 401 having a distal end 402 and a proximal end 404. The cap 400 may also include a bore 406 through which a cartridge 120, such as cartridge 120 in FIG. 1b, is received. In this embodiment, the cap 400 may be partially flexible, and may include a fastening mechanism, such as a pair of arms 408, 410, at the proximal end 404 of the cap 400. The arms 408, 410 may hinge or be flexible, so that they can snap under the ferrule 124 of the cartridge 120, thereby locking the cap 400 to the cartridge 120, in the same manner as retention feature 218 described above with respect to cap 200.

Figure 7:
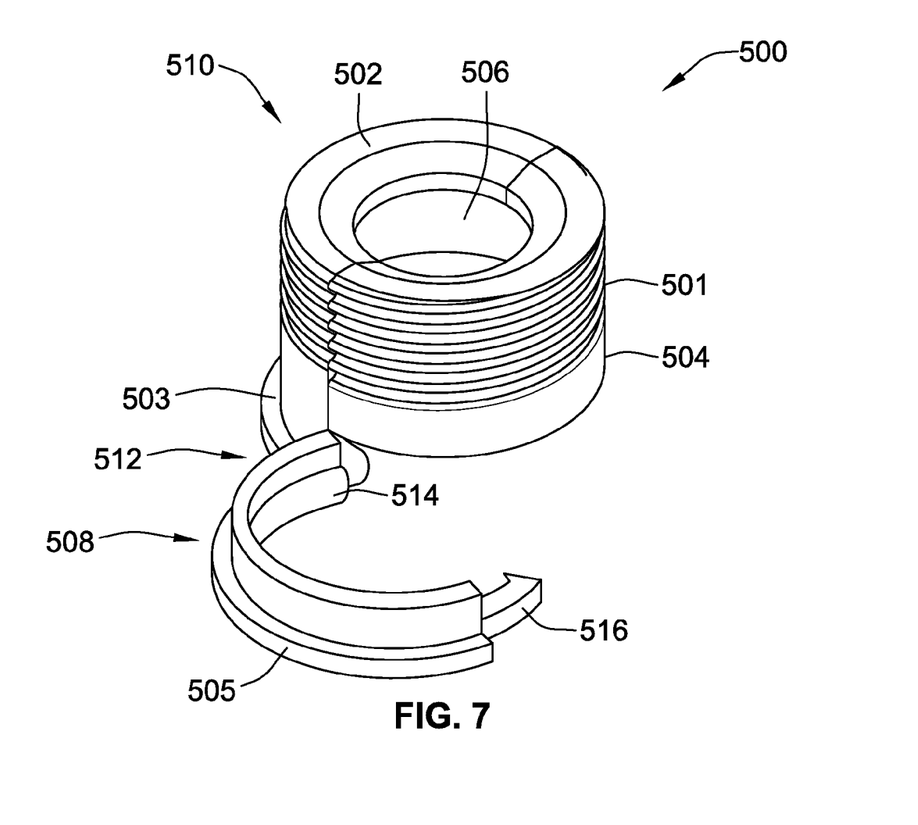
FIG. 7 illustrates yet another embodiment of a cap for use with a cartridge.

FIG. 7 shows yet another embodiment of a cap 500 of the. The cap 500 may include a main body 501 and a bore 506 that extends from a proximal end 508 to a distal end 510 of the cap 500 for surrounding the ferrule 124 of a cartridge 120, such as ferrule 124 of cartridge 120 in FIG. 1b. The cap 500 has an axially extending wall 504 and a flange 503.

Near the proximal end 508, the cap 500 may include a flexible element such as hinge 512.

Also near the proximal end 508, the cap 500 may include a retention feature 514. The retention feature 514 may function in the same manner as retention feature 218 described above with respect to cap 200.

The cap 500 may further include a fastening mechanism to secure the hinged arm 505 to the main body 501. The fastening mechanism may include at least one male element 516 that may be connected to at least one female element (not shown). Although the male element 516 is shown with its hinge 512 at the left hand end, it should be understood that the elements may be reversed. Furthermore, it should be understood that any suitable fastening mechanism may be used to secure the hinged arm 505 to the main body 501.

The disclosed cap system results in a number of advantages. For example, the proposed cap system assists a user to distinguish between medicaments 125, where used with mechanical coding, or colour, to distinguish from drugs without a cap 200, 300, 400, 500 that may not be safe to use with the given drug delivery device 100. This helps to ensure that a drug delivery device 100 can only be used with a medicament 125 for which the drug delivery device 100 is intended. Therefore, with the proposed cap system applied to a cartridge 120, the cartridge 120 is prevented from being loaded into any other drug delivery device 100 by loading a cartridge 120 with an incorrect or unwanted interface. The cap system prevents a user from completing one or more of the following actions: fully inserting the cartridge 120 into an incorrect cartridge holder 104 or attaching the cartridge 120 and/or cartridge holder 104 onto an incorrect dose setting mechanism 102.

The cap system also results in a low cost mechanism since the system does not require a large number of parts and can be manufactured in a cost effective manner. Moreover, there are quite a large number of different cap configurations that may be used. Consequently, with proposed cap system, a large number of medicaments 125 can be distinguished from one another. In addition, with the cap system, if a user attempts to load an incorrect reservoir or cartridge 120 into a cartridge holder 104 designed for a different cartridge 120, the user will be alerted at an early stage of the assembly process.

Exemplary embodiments have been described. However, as those of skill in the art will recognize certain changes or modifications to such arrangements may be made. As just one example, features discussed herein may be taken from one arrangement and combined with features of other arrangements. Those skilled in the art will understand, however, that changes and modifications may be made to these arrangements without departing from the true scope and spirit of the present invention, which is defined by the claims.

The invention claimed is:

1. A cartridge adaptor comprising:
a main body having a proximal end, a distal end, and a bore configured to receive a cartridge containing a medicament and having a bead at the distal end, the main body further comprising a first segment attached to a second segment by a hinge that extends along at least a portion of a length of the main body from the proximal end to the distal end or along a chord on the distal top of the main body, and a retention feature on the main body comprising a protrusion located within the bore and suitable for snapping under the bead of the cartridge for securing the cartridge adaptor to the cartridge;
wherein an outer surface of the first segment comprises a first outer threaded portion and an outer surface of the second segment comprises a second outer threaded portion.

2. The cartridge adaptor of claim 1 wherein the hinge extends along a radius on the distal top of the main body.

3. The cartridge adaptor of claim 1 wherein a proximal portion of the main body is moveable with respect to a distal portion of the main body.

4. The cartridge adaptor of claim 1 wherein the hinge is located at the proximal end of the main body.

5. The cartridge adaptor of claim 1 wherein the retention feature is a protrusion.

6. The cartridge adaptor of claim 1 comprising at least one fastening mechanism for securing the first segment to the second segment.

7. The cartridge adaptor of claim 6 wherein the fastening mechanism comprises a male element and a female element.

8. The cartridge adaptor of claim 1 further comprising a first coding feature that cooperates with a corresponding second coding feature of a drug delivery device, which enables securing the cartridge.

9. The cartridge adaptor of claim 1, wherein the main body further comprises a thread configured for receiving a threaded needle hub, wherein the thread comprises the first threaded portion and the second threaded portion.

10. The cartridge adaptor of claim 1 wherein the retention feature is provided on the proximal end of the main body.

11. The cartridge adaptor of claim 1 wherein the first segment comprises a first threaded portion and the second segment comprises a second threaded portion.

12. The cartridge adaptor of claim 1 wherein the first segment and the second segment comprise a unitary main body.

13. A drug delivery device comprising:
a dose setting mechanism;
a cartridge holder secured to the dose setting mechanism;
a cartridge contained within the cartridge holder; and
a cartridge adaptor secured to the cartridge, the cartridge adaptor comprising a main body having a proximal end, a distal end, and a bore extending from the proximal end to the distal end, the bore being configured to receive the cartridge containing a medicament and having a bead at the distal end, the main body further comprising a first segment attached to a second segment by a hinge that extends along at least a portion of a length of the main body from the proximal end to the distal end or along a chord on the distal top of the main body, and a retention feature on the main body comprising a protrusion located within the bore and suitable for snapping under the bead of the cartridge for securing the cartridge adaptor to the cartridge, wherein the retention feature has an inner dimension that is smaller than an outer dimension of the bead, wherein the first segment comprises a first threaded portion and the second segment comprises a second threaded portion.

14. The drug delivery device of claim 13 wherein the hinge extends along a radius on the distal top of the main body.

15. The drug delivery device of claim 13 wherein a proximal portion of the main body is moveable with respect to a distal portion of the main body.

16. The drug delivery device of claim 13 wherein the hinge is located at the proximal end of the main body.

17. The drug delivery device of claim 13 comprising at least one fastening mechanism for securing the first segment to the second segment.

18. The drug delivery device of claim 17 wherein the fastening mechanism comprises a male element and a female element.

19. The drug delivery device of claim 13 further comprising a first coding feature that cooperates with a corresponding second coding feature of a drug delivery device, which enables securing the cartridge.

20. The drug delivery device of claim 13, wherein the main body further comprises a thread configured for receiving a threaded needle hub, wherein the thread comprises the first threaded portion and the second threaded portion.

21. The drug delivery device of claim 13 wherein the retention feature is provided on the proximal end of the main body.

22. The drug delivery device of claim 13 wherein the first segment and the second segment comprise a unitary main body.

* * * * *